(12) United States Patent
Harper

(10) Patent No.: US 7,070,579 B1
(45) Date of Patent: Jul. 4, 2006

(54) DEVICE USED TO CONNECT AN EXTERNAL VENTRICULAR DRAINAGE CATHETER

(75) Inventor: Derek J. Harper, Santa Ynez, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/070,269

(22) Filed: Apr. 30, 1998

(51) Int. Cl.
  A61M 5/00 (2006.01)
  A61M 5/178 (2006.01)
  A61B 5/14 (2006.01)

(52) U.S. Cl. .......................... 604/167.06; 604/165.03; 600/579

(58) Field of Classification Search ................ 604/174, 604/177, 533, 534, 535, 538, 905, 257
See application file for complete search history.

(56) References Cited

U.S. PATENT DOCUMENTS

| 3,385,553 A | | 5/1968 | Braun | |
|---|---|---|---|---|
| 3,782,383 A | * | 1/1974 | Thompson et al. | 604/177 |
| 3,906,946 A | * | 9/1975 | Nordstrom | 604/177 |
| 3,957,082 A | * | 5/1976 | Fuson et al. | 604/174 |
| 4,161,177 A | * | 7/1979 | Fuchs | 604/177 |
| 4,326,519 A | * | 4/1982 | D'Alo et al. | 604/165.04 |
| 4,897,082 A | * | 1/1990 | Erskine | 604/180 |
| 5,149,330 A | * | 9/1992 | Brightbill | 604/533 |
| 5,356,381 A | | 10/1994 | Ensminger et al. | |
| 5,405,339 A | * | 4/1995 | Kohnen et al. | 604/905 |
| 5,676,656 A | * | 10/1997 | Brimhall | 604/165.03 |
| 5,697,914 A | * | 12/1997 | Brimhall | 604/177 |
| 5,797,869 A | * | 8/1998 | Martin et al. | 604/535 |
| 5,935,110 A | * | 8/1999 | Brimhall | 604/167.06 |

FOREIGN PATENT DOCUMENTS

| FR | 1.336.359 | 8/1963 |
|---|---|---|
| WO | 92/18193 | 10/1992 |
| WO | 99/56814 | 11/1999 |

OTHER PUBLICATIONS

Medtronic PS Medical, "Becker® External Drainage & Monitoring System", 1998.

* cited by examiner

*Primary Examiner*—Nicholas D. Lucchesi
*Assistant Examiner*—Roz Maiorino
(74) *Attorney, Agent, or Firm*—Banner & Witcoff, Ltd.

(57) ABSTRACT

A luer connector is described that is angled away from the patient's scalp in the direction of the drip assembly line. In the preferred embodiment, the luer connector has a female luer connector that mates with a male luer connector on the drip assembly line. The luer connector also has a hollow protrusion that extends into a catheter thereby allowing the luer connector to be fluidly connected to the catheter. A fluid passage is formed through the angled luer connector from the female luer connector, through the body of the angled luer connector and through the hollow protrusion. The luer connector has a pair of "wings" that extend outwardly from the luer connector and allow the luer connector to be sutured to the patient's scalp.

28 Claims, 2 Drawing Sheets

DEVICE USED TO CONNECT AN EXTERNAL VENTRICULAR DRAINAGE CATHETER

BACKGROUND OF THE INVENTION

1. Field of the Invention

This invention relates to a device for connecting a catheter to tubing for draining excess cerebrospinal fluid from the brain.

2. Description of Related Art

It is common medical practice to drain excess cerebrospinal fluid from the brain in cases of hydrocephelus or trauma to the brain. This is commonly done by inserting a catheter into the ventricles of the brain by a process called a ventriculostomy. The catheter is typically made of silicone. An example of such a catheter is the model 46118 EDM Ventricular Catheter sold by Medtronic-PS Medical of Goleta, Calif. Excess cerebrospinal fluid is drained through the catheter into a flexible drip assembly line where it is collected and measured in a drip assembly system.

The catheter is connected to the drip assembly line outside the skull of the patient away from the opening placed in the skull for the catheter to pass. An example of such a drip assembly is the model 46128 Becker EDMS Assembly External Drainage and Monitoring System sold by Medtronic-PS Medical of Goleta, Calif.

As shown in FIG. 1, to fix the catheter 2 to the patient's skull, the catheter 2 is typically connected to the drip assembly line 4 of the drip assembly 6 through a luer connector 8 that extends a distance into an inner lumen 10 of catheter 2. The luer connector 8 has an axis 12 that is aligned with the axis 14 of the catheter 2. A silicone "collar" 16 is wrapped around the silicone catheter 2. A portion of the luer connector 8 extends into the catheter 2. Collar 16 is sutured to the patient's scalp 18. The stickiness of the two silicone pieces, catheter 2 and collar 16, keeps the catheter 2 from moving relative to the collar 16.

The axis 12 of luer connector 8 may run parallel to the patient's scalp 18 making it difficult to connect the drip assembly line 4 to the luer connector 8. This problem occurs because there is no clearance between the luer connector 8 and the patient's scalp 18. In addition, because there are separate elements for luer connector 8 and collar 16, additional time is required to separately configure the luer connector 8 and collar 16. Further, these types of prior art connectors rely on the inherent stickiness of the silicone to silicone contact to maintain the relative positions of the catheter 2 and the collar 16. It is possible that this inherent stickiness may be compromised in an operating room environment. These are problems in want of a solution.

SUMMARY OF THE INVENTION

A luer connector is described that is angled away from the patient's scalp in the direction of the drip assembly line. In the preferred embodiment, the luer connector has a female luer connector that mates with a male luer connector on the drip assembly line. The luer connector also has a hollow protrusion that extends into a catheter thereby allowing the luer connector to be fluidly connected to the catheter. A fluid passage is formed through the angled luer connector from the female luer connector, through the body of the angled luer connector and through the hollow protrusion. The luer connector has a pair of "wings" that extend outwardly from the luer connector and allow the luer connector to be sutured to the patient's scalp.

It is a primary object of the present invention to provide a luer connector for connecting a catheter to a drip assembly line that allows the medical practitioner to easily and reliably connect the drip assembly line to the catheter connector.

It is another object of the present invention to provide a luer connector for connecting a catheter to a drip assembly line that consolidates the features of a luer connector and a collar into a single unit.

These and other object of the present invention will be clear with reference to the description contained herein and more particularly with reference to the following detailed description of the invention and the accompanying drawings. Throughout the description, like elements are referred to by like reference numbers.

DETAILED DESCRIPTION OF THE INVENTION

Figure 1:
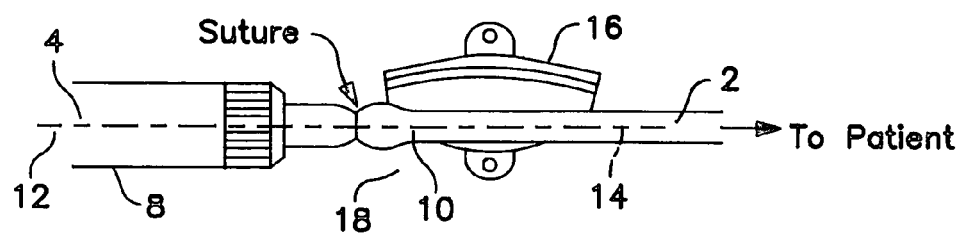
FIG. 1 is a top view of a prior art collar and luer connector with the collar in an open position.
Figure 2:
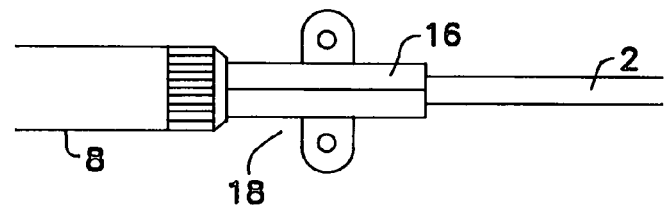
FIG. 2 is a top view of the prior art collar and luer connector of FIG. 2 with the collar of FIG. 1 in a closed position around the catheter.
Figure 3:
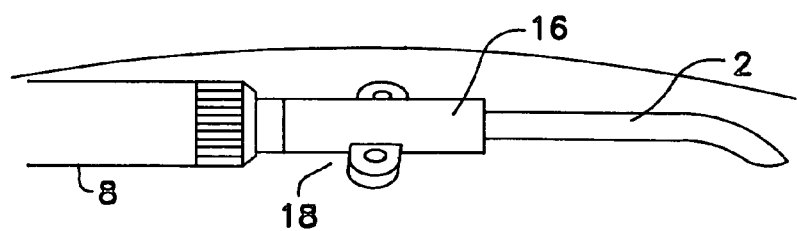
FIG. 3 is a perspective view of the prior art collar and luer connector of FIG. 2.
Figure 4:
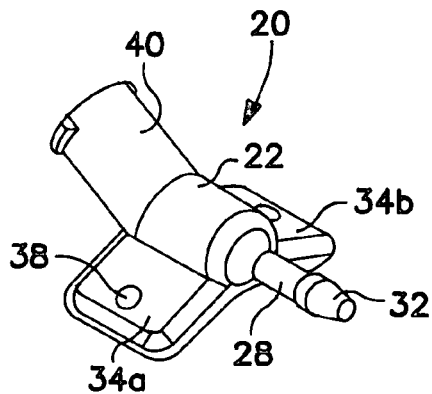
FIG. 4 is a perspective view of the angled luer connector of the present invention.
Figure 5:
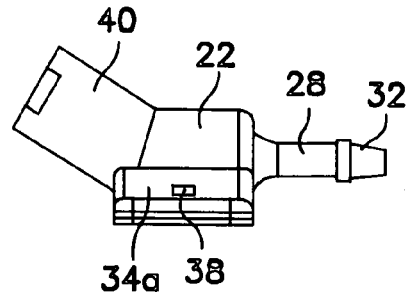
FIG. 5 is a side view of the angled luer connector of FIG. 4.
Figure 6:
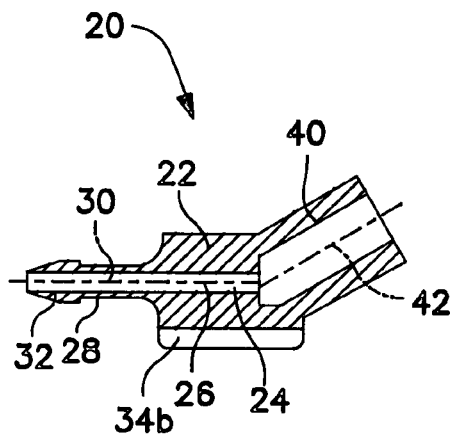
FIG. 6 is a cross-sectional side view of the luer connector of FIG. 4.
Figure 7:
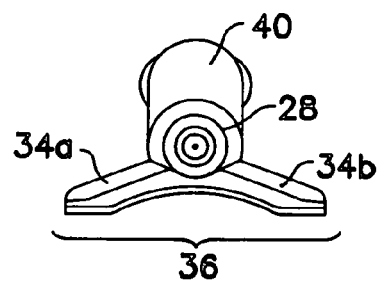
FIG. 7 is an end view of the angled luer connector of FIG. 4.
Figure 8:
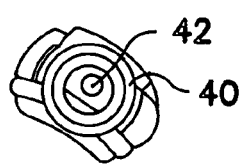
FIG. 8 is an end view of the angled luer connector of FIG. 4.
Figure 9:
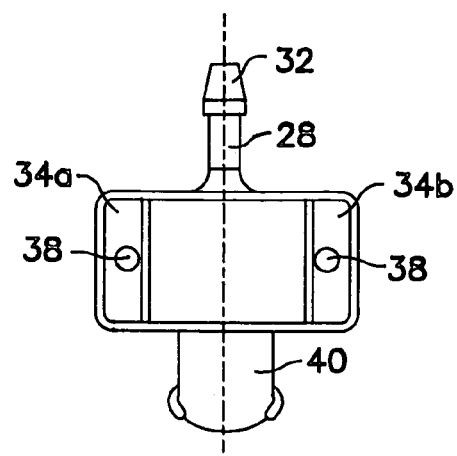
FIG. 9 is a bottom view of the angled luer connector of FIG. 4.

The angled luer connector is shown in the Figures generally labeled 20. Angled luer connector 20 includes a central hollow barrel 22 having a barrel lumen 24. Barrel 22 has a barrel axis 26 that is coaxial with barrel lumen 24.

A hollow catheter connection protrusion 28 is attached to and extends away from barrel 22. Catheter connection protrusion 28 has a protrusion lumen 30 that extends through catheter connection protrusion 28. In the preferred embodiment, protrusion lumen 30 is coaxial with barrel lumen 24. Catheter connection protrusion 28 has an outside diameter that allows it to be firmly inserted into the inner lumen 10 of catheter 2. To more firmly seat catheter connection protrusion 28 within the inner lumen 10 of catheter 2, a bulbous end 32 is formed on the end of catheter connection protrusion 28. Bulbous end 32, at its greatest diameter, has a slightly larger diameter than the majority of catheter connection protrusion 28.

Angled luer connector 20 has a pair of substantially planar, wing-like anchoring protrusions 34a,b that extend away from barrel 22. Together, anchoring protrusions 34a,b form a substantially planar platform 36 to contact the patient's scalp 18. This prevents the angled luer connector 20 from rotating about the axis 26 and firmly locates the angled luer connector 20 on the patient's scalp 18. Each anchoring protrusion 34 has a suture hole 38 that allows the anchoring protrusions 34*a*,*b*, and consequently the angled luer connector 20, to be firmly anchored to the patient's scalp 18.

A female luer connector 40 is attached to barrel 22 opposite protrusion 28. Female luer connector 40 has a female luer axis 42 that is not coaxial with axis 26. In the preferred embodiment, axis 42 intersects axis 26 at an angle of about 30°. The 30° angle between axis 42 and axis 26 is oriented so that axis 42 also forms about a 30° angle to the substantially planar platform 36. In this way, when angled luer connector 20 is sutured to a patient's scalp 18 as described below, female luer connector 40 is directed away from the patient's scalp 18.

In the preferred embodiment, female luer axis 42 is equidistant from each of the anchoring protrusions 34*a*,*b*. However, in an alternate embodiment, female luer axis 42 may be rotated around its intersection with barrel axis 26 so that it is closer to one of the anchoring projections 34*a*,*b* than the other.

Although the preferred angle between central axis 42 and axis 26 is about 30°, any angle between central axis 42 and axis 26 that allows female luer connector 40 to be directed away from the patient's scalp 18 is within the invention. In particular, it is anticipated that an angle as low as 15° or as high a 90° between central axis 42 and axis 26 is within the scope of the invention.

Female luer connector 40 is threaded and allows a male luer connector of corresponding threads to be mated with female luer connector 40 as is well understood in the art. Female luer connector 40 is in fluid communication with barrel lumen 24 so that fluid entering the female luer connector 40 through the interconnection between female luer connector 40 and a male luer connector passes into barrel lumen 24. Because female luer connector 40 is angled away from the patient's scalp as described above, the physician will be able to more easily connect the male luer connector to the female luer connector 40.

Although the preferred embodiment has a female luer connector 40 connected to barrel 22, it is also within the scope of the invention for other connectors to be attached to barrel 22 for connecting angled luer connector 20 to a drip assembly line 4. This would include replacing female luer connector 40 with a male luer connector. Of course, a female luer connector would then need to be placed on the drip assembly line 4. Other connectors and connecting systems will occur to those skilled in the art.

Preferably, angled luer connector 20 is made of a rigid thermo-plastic such as polycarbonate, polypropylene, polyoxymethylene, PET, nylon, styrene or acrylic. Alternately, angled luer connector 20 can be made of metal, ceramic or almost any other semi-rigid thermo-plastic or thermoset material.

In use, a physician will insert catheter 2 into the patient's ventricle by performing a ventriculostomy. The proximal end of catheter 2 will extend outside of the patient's skull. The physician will insert catheter connection protrusion 28 into the inner lumen 10 of catheter 2. Bulbous end 32 assists in retaining catheter connection protrusion 28 in the inner lumen 10 of catheter 2. The physician will typically place a suture around catheter 2 and protrusion 28 to more securely hold catheter 2 in position on catheter connection protrusion 28.

Anchoring protrusions 34*a*,*b* are sutured to the patient's scalp 18 through suture holes 38. The male luer connector from the drip assembly line 4 is connected to female luer connector 40. Excess cerebrospinal fluid then passes from the ventricle, through the inner lumen 10 of catheter 2 to angled luer connector 20 where is passes to drip assembly line 4 to ultimately be collected and measured in drip assembly 6.

The invention has been described in connection with a specific embodiments. It will be clear to those skilled in the art that changes and modifications may be made to the description given herein and still fall within the scope of the invention as claimed in the following claims. Further, obvious modifications and changes to the description will occur to those skilled in the art that will still fall within the claims.

I claim:

1. A bodily fluid drainage assembly having a catheter in the body and a luer connector for connecting the catheter to a drip assembly line comprising:
    a hollow barrel having a barrel lumen, the barrel having a barrel axis that is coaxial with the barrel lumen, the hollow barrel having a single terminal;
    a hollow catheter connection protrusion attached to and extending away from the barrel, the catheter connection protrusion sized to fit within the catheter, the catheter connection protrusion having a protrusion lumen that extends through the catheter connection protrusion, the protrusion lumen being in fluid communication with the barrel lumen, the catheter connection protrusion having a terminal end opposite the barrel;
    a pair of anchoring protrusions attached to and extending away from the barrel, the anchoring protrusions being formed essentially in a plane:
    a female luer connector attached to the barrel opposite the catheter connection protrusion, the female luer connector creating the single terminal, the female luer connector having a female luer axis that extends through and is coaxial with the female luer that is not coaxial with the barrel axis, the female luer axis extending away from the plane containing the anchoring protrusions.

2. The assembly of claim 1 wherein the female luer axis intersects the barrel axis at an angle of between 15° to 90°.

3. The assembly of claim 2 wherein the female luer axis intersects the barrel axis at an angle of about 30°.

4. The assembly of claim 1 wherein the pair of anchoring protrusions produce a substantially planar surface.

5. The assembly of claim 4 wherein the female luer axis intersects the substantially planar surface.

6. The assembly of claim 1 wherein the female luer axis is equidistant from each of the anchoring protrusions.

7. The assembly of claim 1 wherein the female luer axis is closer to one of the anchoring protrusions than the other.

8. The assembly of claim 1 wherein the anchoring protrusions each have a suturing hole to allow the anchoring protrusions to be attached to a patient.

9. The assembly of claim 1 wherein the protrusion lumen is coaxial with the central lumen.

10. The assembly of claim 1 wherein the protrusion has an outside diameter that of slightly larger diameter than the inner lumen of the catheter.

11. The assembly of claim 1 further comprising a bulbous end formed on the terminal end of the catheter connection protrusion.

12. A bodily fluid drainage assembly having a catheter in the body and a luer connector for connecting the catheter to drip assembly line comprising:
    a hollow barrel having a barrel lumen, the barrel having a barrel axis that is coaxial with the barrel lumen, the hollow barrel having a single terminal;
    a hollow catheter connection protrusion attached to and extending away from the barrel, the catheter connection protrusion sized to fit within the catheter, the catheter connection protrusion having a protrusion lumen that extends through the catheter connection protrusion, the protrusion lumen being in fluid communication with the barrel lumen;

a pair of anchoring protrusions attached to and extending away from the barrel, the pair of anchoring protrusions producing a substantially planar surface;

a female luer connector attached to the barrel opposite the catheter connection protrusion, the female luer connector creating the single terminal, the female luer connector having a female luer axis that extends through and is coaxial with the female luer that is not coaxial with the barrel axis, the female luer axis extending away from the plane containing the anchoring protrusions, the female luer axis intersecting the barrel axis at an angle of about 30°.

13. The assembly of claim 12 wherein the female luer axis is equidistant from each of the anchoring protrusions.

14. The assembly of claim 12 wherein the female luer axis is closer to one of the anchoring protrusions than the other.

15. The assembly of claim 12 wherein the anchoring protrusions each have a suturing hole to allow the anchoring protrusions to be attached to a patient.

16. A bodily fluid drainage assembly having a catheter in the body and a luer connector for connecting a catheter to a drip assembly line comprising:

a hollow barrel having a barrel lumen, the barrel having a barrel axis that is coaxial with the barrel lumen, the hollow barrel having a single terminal;

a hollow catheter connection protrusion attached to and extending away from the barrel, the catheter connection protrusion sized to fit within the catheter, the catheter connection protrusion having a protrusion lumen that extends through the catheter connection protrusion, the protrusion lumen being in fluid communication with the barrel lumen;

a pair of anchoring protrusions attached to and extending away from the barrel, the pair of anchoring protrusions producing a substantially planar surface;

a female luer connector attached to the barrel opposite the catheter connection protrusion, the female luer connector creating the single terminal, the female luer connector having a female luer axis that extends through and is coaxial with the female luer that is not coaxial with the barrel axis or coplanar with the substantially planar surface of the pair of anchoring protrusions, the female luer axis intersecting the barrel axis at an angle of about 30°.

17. The assembly of claim 16 wherein the female luer axis is equidistant from each of the anchoring protrusions.

18. The assembly of claim 16 wherein the female luer axis is closer to one of the anchoring protrusions than the other.

19. A bodily fluid drainage assembly having a catheter in the body and a connector for connecting a catheter drip assembly line comprising:

a hollow barrel having a barrel lumen, the barrel having a barrel axis and a single terminal;

a hollow catheter connection protrusion attached to and extending away from the barrel, the catheter connection protrusion sized to fit within the catheter, the catheter connection protrusion having a protrusion lumen that extends through the catheter connection protrusion, the protrusion lumen being in fluid communication with the barrel lumen;

means for attaching the connector to a patient's scalp, the means for attaching being formed essentially in a plane;

means for fluidly connecting a drip assembly to the barrel opposite the catheter connection protrusion, the means for fluidly connecting being elongated along an axis that is coaxial with the means for fluidly connecting and that is not coaxial with the barrel axis or coplanar with the plane of the means for attaching, the means creating the single terminal.

20. A bodily fluid drainage assembly having a catheter in the body and a connector for connecting a catheter to a drip assembly for a patient comprising:

a first conduit having a first lumen, the first conduit having a first axis coaxial with the first lumen, the first conduit having a single terminal;

a second conduit having a second lumen, the second lumen in fluid communication with the first lumen, the second conduit having a second axis coaxial with the second lumen, the second axis intersecting the first axis but not being coaxial with the first axis and extending away from the patient's body, the second conduit creating the single terminal of the first conduit;

means for connecting the first conduit to the catheter;

means for connecting the second conduit to the drip assembly;

means for connecting the connector to a patient's scalp, the means for connecting being formed essentially in a plane; and the second axis not coplanar with the plane of the means for connecting.

21. The assembly of claim 20 wherein the second axis intersects the first axis at an angle of between 15° to 90°.

22. The assembly of claim 21 wherein the second axis intersects the first axis at an angle of about 30°.

23. The assembly of claim 20 wherein the means for connecting are a pair of anchoring protrusions extending away from the connector.

24. The assembly of claim 23 wherein the pair of anchoring protrusions produce a substantially planar surface.

25. The assembly of claim 24 wherein the second axis intersects the substantially planar surface.

26. The assembly of claim 23 wherein the second axis is equidistant from each of the anchoring protrusions.

27. The assembly of claim 23 wherein the second axis is closer to one of the anchoring protrusions than the other.

28. The assembly of claim 23 wherein the anchoring protrusions each have a suturing hole to allow the anchoring protrusions to be attached to a patient.

* * * * *